(12) United States Patent
Tsai et al.

(10) Patent No.: US 8,583,207 B2
(45) Date of Patent: Nov. 12, 2013

(54) AUDIO/VIDEO RECORDING METHOD AND DEVICE

(75) Inventors: Jang-Zern Tsai, Jung-Li (TW);
Cheng-Deng Kuo, Taipei (TW);
Ssu-Hsien Chuang, Taipei (TW);
Ping-Hsiang Tsai, Sanchong (TW)

(73) Assignee: National Central University, Taoyuan County (TW)

( * ) Notice: Subject to any disclaimer, the term of this patent is extended or adjusted under 35 U.S.C. 154(b) by 856 days.

(21) Appl. No.: 12/264,861

(22) Filed: Nov. 4, 2008

(65) Prior Publication Data
US 2009/0226150 A1 Sep. 10, 2009

(30) Foreign Application Priority Data
Mar. 5, 2008 (TW) ................... 97107695 A

(51) Int. Cl.
*A61B 5/05* (2006.01)
(52) U.S. Cl.
USPC ........... 600/407; 600/586; 600/508; 600/118; 600/200; 600/533; 600/538

(58) Field of Classification Search
USPC .......... 386/239, 232, 287, 248; 600/407, 586, 600/508, 118, 200
See application file for complete search history.

(56) References Cited

U.S. PATENT DOCUMENTS

| | | | |
|---|---|---|---|
| 2006/0051062 A1* | 3/2006 | Kusaka et al. | 386/95 |
| 2008/0106614 A1* | 5/2008 | Okuda et al. | 348/231.2 |
| 2009/0203986 A1* | 8/2009 | Winnick | 600/407 |

* cited by examiner

*Primary Examiner* — Helen Shibru
(74) *Attorney, Agent, or Firm* — Chun-Ming Shih

(57) ABSTRACT

An audio/video recording method and device for recording a main audio/video file and at least one index audio/video file corresponding to the main audio/video file. A section of the index audio/video files can be transformed into text data serving as a portion of file names of the main audio/video file. When a user collates or uses the main audio/video file, the index audio/video file is used to accelerate distinguishing what the main audio/video files are, thereby facilitating searching, classification and management of the main audio/video file effectively.

6 Claims, 3 Drawing Sheets

AUDIO/VIDEO RECORDING METHOD AND DEVICE

BACKGROUND

The present invention relates to an audio/video recording method and device, especially to a method to record a main audio/video file and at least one index audio/video file corresponding to the main audio/video file before/after recording the main audio/video file.

There are various digital audio/video recording devices, such as recording sticks, portable MP3 players/recorders, digital cameras, video capture devices, audio and video recorder embedded in mobile phones and so on. Due to their small sizes and large storage capacities, their applications in audio/video recording are becoming more and more popular, such as interviewing recording, class recording, and clinical sound gathering for medical researches and so on.

However, the following difficulties will occur when a user gathers and stores several main audio/video files in a small-size audio/video recording device.

First, when the user records the audio/video signals into main audio/video files in an audio/video recording device, usually the audio/video recording device will assign the filenames for the main audio/video files. The assigned filenames are usually just serial numbers based on the sequence of recording and are irrelevant to the content of the corresponding audio/video files. When a user needs to find a specific file among a number of recorded main audio/video files, he or she will have to listen to the content of the main audio/video files one by one, because the content of the main audio/video files cannot be known from their filenames. Sometimes, the user has to listen to a considerable length of a main audio/video file before he or she can recognize the content of the file. Even worse, sometimes the user may not be able to recognize the content of a main audio/video file after listening to the whole file.

Second, after storing a number of main audio/video files without descriptive filenames, it is inconvenient to recognize and manage these main audio/video files.

Third, even though the recorder may allow the user to enter filenames manually, the number of press buttons is usually incomplete due to limited physical size of the recorder. Some recorders may require the user to follow a complicated procedure to enter filenames, but it usually is time-consuming and may not be suitable in some occasions.

A new audio/video recording technique which overcomes the above problems and can facilitate the management of the main audio/video files stored in an audio/video recording device is desired.

BRIEF SUMMARY

As described above, when a user uses a traditional audio/video recording device to record an audio/video signal into a main audio/video file, several problems will be encountered, including the inconvenience of entering the filename of the recorded file, the difficulty in managing a number of main audio/video files without meaningful filenames, the difficult in recognizing and finding an audio/video file.

A new audio/video recording method and device are proposed in the present invention. The audio/video recording method includes recording at least one index audio/video file before/after recording a main audio/video file. The index audio/video file can be a short message of a scene, a face figure, a person name, an identification number, a place or a recording state. In addition, the method involves using speech input to name a recorded main audio/video file. This is a way of entering filename without being limited by the physical size of the recording device. Furthermore, one section of the index audio/video file can be transformed into text data, and the text data can become a section of a file name of the main audio/video file. The method of the present invention is valuable in the industry, such as companies that produce audio/video recording apparatus, medical instruments, or mobile phones.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

Figure 1:
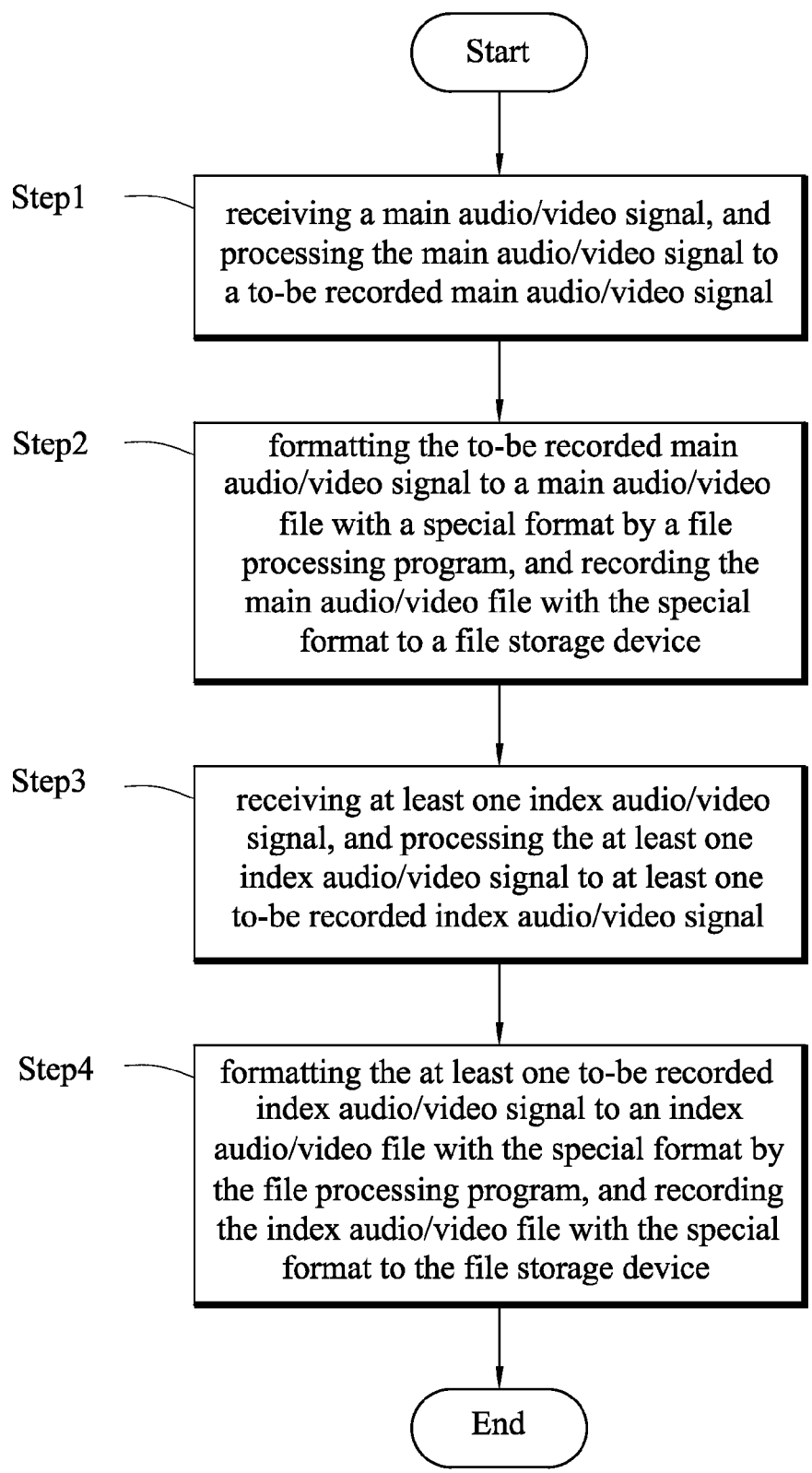
FIG. 1 is a schematic flow chart of an index recording method of a preferred embodiment of the present invention.

An exemplary embodiment of the audio/video recording method and device is provided below. With respect to the audio/video recording method and device, before/after a main audio/video file is recorded, at least one corresponding index audio/video file is established for assisting the classification and management of the main audio/video files. As shown in FIG. 1, this method includes four main steps that can be realized in an audio/video processor. Step 1: receiving a main audio/video signal, and processing the main audio/video signal into a to-be-recorded main audio/video signal; step 2: formatting the to-be-recorded main audio/video signal into a main audio/video file with a special format by a file processing program, and recording the main audio/video file with the special format to a file storage device; step 3: receiving at least one index audio/video signal, and processing the at least one index audio/video signal into at least one to-be-recorded index audio/video signal; step 4: formatting the at least one to-be-recorded index audio/video signal into an index audio/video file with a special format by the file processing program, recording the index audio/video file with the special format to the file storage device.

The above audio/video recording method can further include the following steps: picking up one section of the to-be-recorded index audio/video signal; transforming this section of the to-be-recorded index audio/video signal into text data by a transforming program; and making the text data a section of the file names of the main audio/video file with a special format.

The above audio/video recording method can further include the following steps: picking up one section of the to-be-recorded index audio/video signal; transforming the section of the to-be-recorded index audio/video signal into text data by a transforming program; making the text data a section of the file names of the index audio/video file with a special format.

The above audio/video recording method can further include the following steps: picking up one section of the index audio/video file, transforming the section of the index audio/video file into text data by a transforming program; making the text data a section of the file names of the main audio/video file with a special format.

The above audio/video recording method can further include the following steps: picking up one section of the index audio/video file, transforming the section of the index audio/video file into text data by a transforming program; making the text data a section of the file names of the index audio/video file with a special format.

The index audio/video signal accompanying a main audio/video file must contain messages that can remind a user of the content of the main audio/video file. It can include various categories of information, such as the source of the main audio/video signal, the date and the time when the main audio/video signal is acquired, the name of the person who generates the main audio/video signal, the place where the main audio/video signal is acquired, the purpose of recording the main audio/video signal, a descriptive title of the main audio/video signal, etc.

After a number of main audio/video files are recorded in an audio/video recording device, it may not be easy to find a main audio/video file with specific content. If those files are not properly named, a filenames has no connection with the content of its corresponding file. In that situation, the user has to listen to or view the content of the recorded main audio/video files one by one until the target content is heard or seen. That will be very time consuming because the main audio/video files are usually long. On the other hand, if index audio/video files are also recorded, the user can start by listening to or viewing the content of the index audio/video files, which are much smaller than the main audio/video files.

In a preferred embodiment, the index audio/video signal is a speech signal. The index audio/video signal can be transformed into text data by a speech recognition technique and the text data can become a section of the name of the main audio/video file. Thus, the filename represents an attribute of the content of the main audio/video file.

Figure 2:
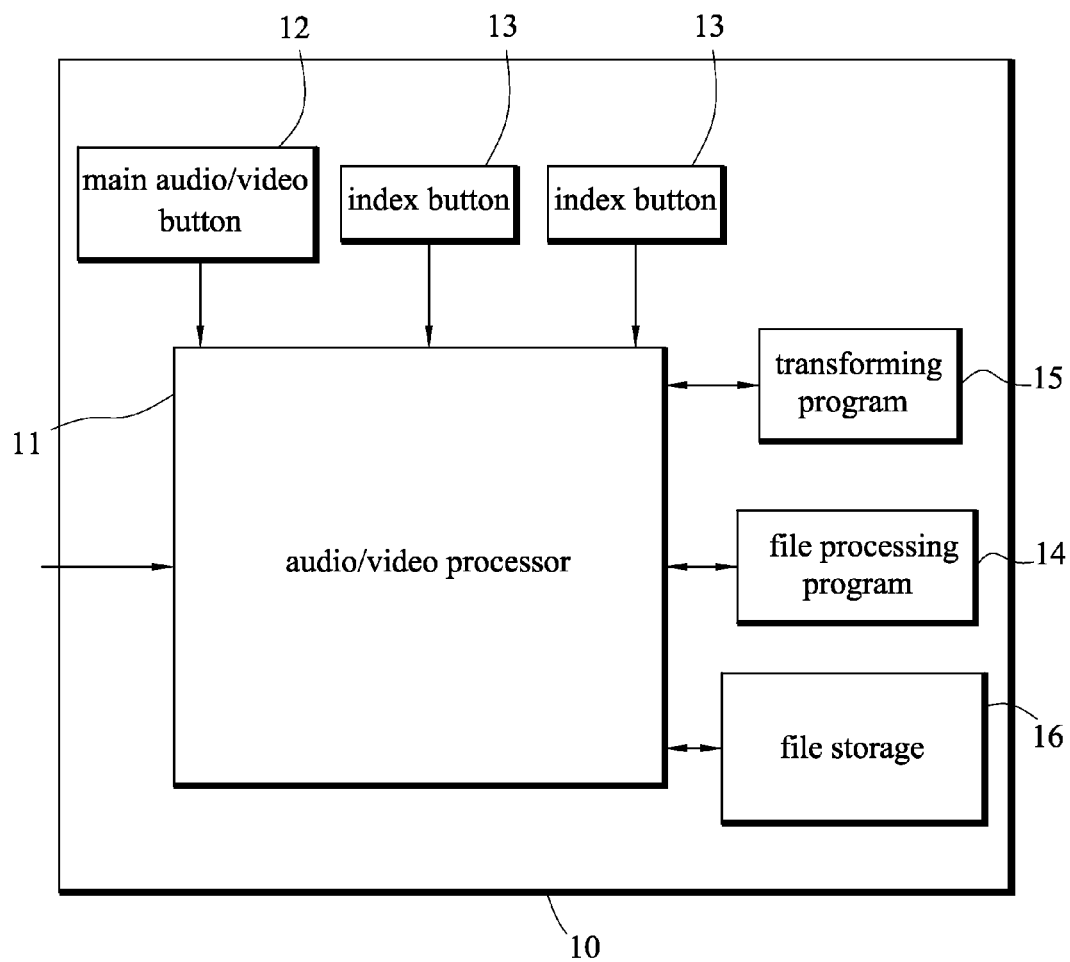
FIG. 2 is the hardware functional block diagram of the index recording device of the preferred embodiment of the present invention.

FIG. 2 shows a schematic flowchart of the index audio/video recording device in accordance with the preferred embodiment. The index audio/video recording device 10 includes an audio/video processor 11, a main audio/video button 12, at least one index button 13, a file processing program 14, a transforming program 15, and a file storage device 16. Device 10 is configured for receiving and processing audio/video signals and storing files. The audio/video processor 11 is for sensing/detecting and processing/transforming a main audio/video signal into a to-be-recorded main audio/video signal, and for sensing/detecting and processing/transforming at least one index audio/video signal into at least one to-be-recorded index audio/video signal. The main audio/video button 12 is for signifying the to-be-recorded main audio/video signal in a recording process. The at least one index button 13 is for signifying the to-be-recorded index audio/video signal in a recording process. The file processing program 14 is for formatting the to-be-recorded main audio/video signal into a to-be-record main audio/video file with a special format, and for formatting the to-be-recorded index audio/video signal into a to-be-record index audio/video file with a special format. The transforming program 15 is for transforming one section of the to-be-recorded index audio/video signal picked by the file processing program 14 into text data. The file storage 16 is for storing the formatted main audio/video file and the index audio/video file.

The file processing program 14 is capable of picking one section of the to-be-recorded index audio/video signal and transforming the section of the to-be-recorded index audio/video signal into text data through the transforming program 15. The text data can further be used as one section of a name of the main audio/video file.

The file processing program 14 is capable of picking one section of the to-be-recorded index audio/video signal, and transforms the section of the to-be-recorded index audio/video signal into text data through the transforming program 15. The text data can further be used as one section of a name of the index audio/video file.

In the preferred embodiment, at least one index button 13 is provided. In operation, the user presses one index button 13 and input an index audio/video signal, and then a corresponding index audio/video file is generated.

The index audio/video recording method of the present invention is especially applicable in portable recording/playback audio/video devices, such as MP3 players and recorders, and so on. Traditionally, it may be impossible to provide a convenient full-text manual input interface on portable audio/video recording devices due to their small sizes. The present invention provides a convenient alternative to this manual input manner.

Figure 3:
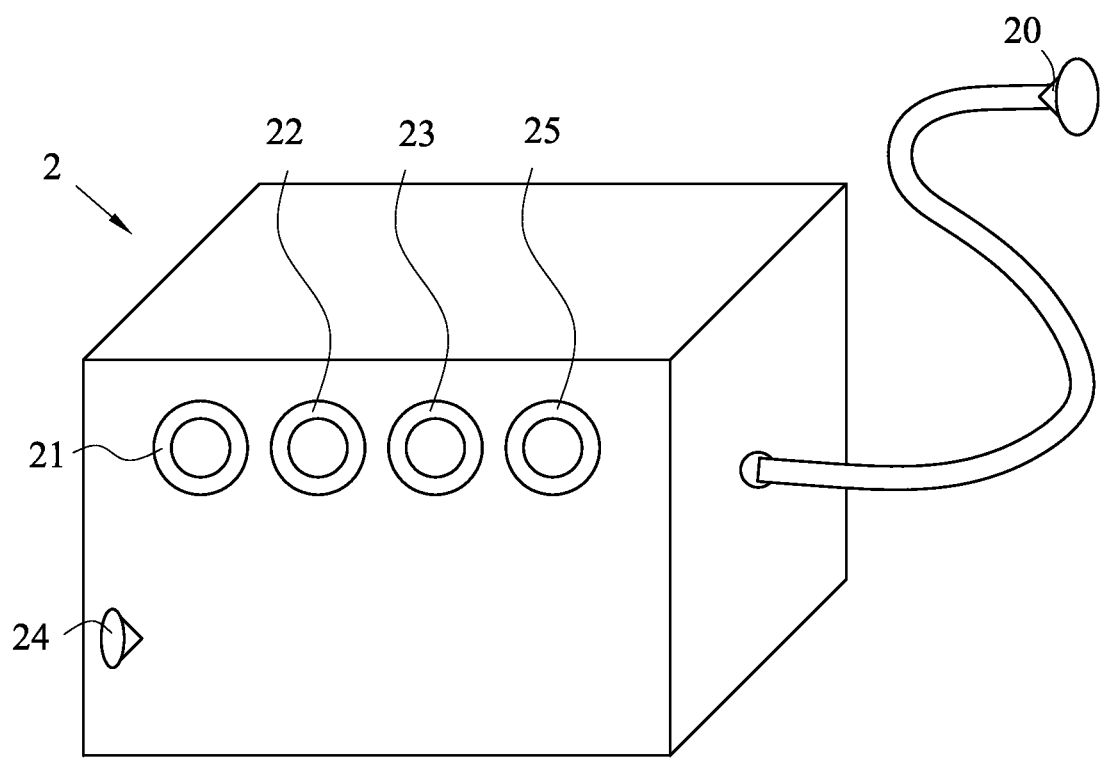
FIG. 3 is a schematic view of the preferred embodiment of the present invention.

Refer to FIG. 3. A digital stethoscope for mass collection of clinical lung sound signals includes a MP3 player/recorder 2 and an electronic stethoscope head 20. The player/recorder 2 includes a first index button 21, a second index button 22 and a third index button 23. When one of the index buttons 21, 22, and 23 is pressed and held in the pressed state, a voice is recorded to be an index file through a microphone 24 of the player/recorder 2. Before a user collects a lung sound signal, the first index button 21 is pressed and held in the pressed state while the patient's identification number is being input by the user through the microphone 24 of the player/recorder 2; the second index button 22 is pressed and held in the pressed state while the current date and time is being input by the user through the microphone 24 of the player/recorder 2; the third index button 23 is pressed and held in the pressed state while the patient's condition is being input by the user through the microphone 24 of the player/recorder 2. A patient's condition includes "normal", "asthma attack", and "after asthma attack". The main audio/video button 25 of the player/recorder 2 is pressed and the electronic stethoscope head 20 is used to acquire the lung sound signal of the patient to be recorded as a lung sound file. In such a fashion, a number of lung sound files can be collected from a number of patients and can be stored in the player/recorder 2. These lung sound files can be transferred from the portable player/recorder 2 to a hospital data system for the doctors and nurses to trace a lung pathological process of each patient. Usually, files of an individual patient are stored in his or her special folder in the hospital data system. Before a lung sound file is stored in the hospital data system, the first index file corresponding to the lung sound file is listened to in order to determine which patient the lung sound belongs to and which folder that file should be stored in. The second index file can be use to find the lung sound recorded at a specific time interval. The third index file can be used to group the recorded lung sound files according to patients' conditions.

Compared with traditional techniques, the present audio/video recording method and device have the following advantages.

First, in traditional audio/video recording devices, especially portable ones, usually no proper filenames are given to main audio/video files. Without meaningful filenames, it is time-consuming and difficult to try to find a target audio/video file among a large number of stored main audio/video files. In the present invention, at least one index audio/video file can be recorded with a short audio/video message relevant to the content of the corresponding main audio/video file. This way, by listening to or viewing the index audio/video files, the user can find the target file more easily.

Second, attempting to provide manual inputting function for portable audio/video player/recorder always faces a size-limitation problem. As the portable audio/video player/recorder becomes smaller and smaller in physical size, the space for press buttons also becomes smaller and smaller. With the present invention, recording of index audio/video signals is virtually independent of the physical size of the audio/video recorders.

Third, the present invention enables generation of descriptive filenames. In the present invention, the content of an index audio/video file can further be recognized by audio/video recognition method and transformed into text data. The text data can become one section of the name of the main audio/video file. Therefore, the present invention facilitates the generation of descriptive filenames, which are more meaningful to the users than traditional serial-number filenames are.

The portable audio/video recorder devices (such as MP3 players/recorders) has a small size, and can not provide convenient and whole text input interface. The present invention is especially suitable for this type of applications. The index audio/video file contains an attribute of the main audio/video file so that it can effectively facilitate searching, classification and management of the main audio/video file.

In application, the method of the present invention is used in some valuable related industry, such as apparatus companies, medical equipment companies, MP3-production companies or mobile phone manufacturers and so on.

The above description is given by way of example, and not limitation. Given the above disclosure, one skilled in the art could devise variations that are within the scope and spirit of the invention disclosed herein, including configurations ways of the recessed portions and materials and/or designs of the attaching structures. Further, the various features of the embodiments disclosed herein can be used alone, or in varying combinations with each other and are not intended to be limited to the specific combination described herein. Thus, the scope of the claims is not to be limited by the illustrated embodiments.

What is claimed is:

1. A digital stethoscope for mass collection of clinical lung sound signals, comprising:
   a stethoscope head; and
   an audio recording and playing device including:
   a main button;
   at least one index button;
   a processor for receiving a main signal when the main button is pressed and held for recording, and for receiving at least one index signal when the at least one is pressed and held for recording;
   a file processing program for formatting the main signal into a main file with a special format, and for formatting the at least one index signal into an index file with a special format;
   a transforming program for transforming one section of the at least one index signal picked by the file processing program into text data; and
   a file storage for storing the main file and the index file,
   wherein after the at least one index button is pressed and held to record a patient's identification number, a current date and time, or a patient's condition, the main button is pressed and held and the stethoscope head is used for acquiring the main signal of a patient.

2. The digital stethoscope as claimed in claim 1, wherein the text data serves as one section of a name of the main file.

3. The digital stethoscope as claimed in claim 1, wherein the text data serves as one section of a name of the at least one index file.

4. The digital stethoscope as claimed in claim 1, wherein there are a first index button, a second index button and a third index button to respectively record the patient's identification number, the recorded date and time, and the patient's condition.

5. The digital stethoscope as claimed in claim 4, wherein the main signal is a lung sound signal to be formatted as a lung sound file.

6. The digital stethoscope as claimed in claim 5, wherein there are lung sound files transferred to a hospital data system for doctors and nurses to trace a lung pathological process of each patient, before the lung sound file is stored, the first index file corresponding to the lung sound file is listened to in order to determine which patient the lung sound belongs to and which folder that lung sound file should be stored in, the second index file is used to find the lung sound file recorded at a specific time interval, and the third index file is used to group the lung sound files according to the patient's condition including normal, asthma attack or after asthma attack.

* * * * *